United States Patent [19]

Staple et al.

[11] Patent Number: 5,039,619
[45] Date of Patent: Aug. 13, 1991

[54] METHOD FOR DETECTING CHARACTERISTIC MARKERS OF DISEASE IN BIOLOGICAL FLUIDS

[75] Inventors: Peter H. Staple, Amherst; Chester DeLuca, Williamsville, both of N.Y.; Stephen J. Millar, Houston, Tex.

[73] Assignee: State University of New York, Albany, N.Y.

[21] Appl. No.: 410,089

[22] Filed: Sep. 20, 1989

[51] Int. Cl.$^5$ .............................................. G01N 21/77
[52] U.S. Cl. ........................................ 436/164; 424/3; 424/7.1; 436/63; 436/64; 436/86; 436/94; 436/169
[58] Field of Search ............... 436/94, 64, 86, 164, 436/63, 183, 169; 424/3, 7.1

[56] References Cited

U.S. PATENT DOCUMENTS 4,468,465  8/1984  Sato ..................................... 436/64

OTHER PUBLICATIONS

Scott et al., "Differential Staining of Polyanions According to Critical Electrolyte Concentration of Principles in Mixed Solvents", *Journal of Microscopy*, vol. 129, Pt. 2, pp. 209-219, Feb. 1983.
Orford et al., "Ultrastructural Alterations in Glycosaminoglycans of Dog Femoral Condylar Cartilage After Surgical Division of an Anterior Cruciate Ligament: a Study with Cupromeronic Blue in a Critical Electrolyte Concentration Technique", *Journal of Anatomy*, vol. 148, pp. 233-244, 1986.
"Glycosaminoglycans in Human Gingival Crevicular Fluid as Indicators of Active Periodontal Disease," K. S. Last, J. B. Stanbury and G. Embery, *Archives of Oral Biology*, vol. 30, No. 3, pp. 275-281 (1985).
"Characterization of Glycosaminogylcan-Alcian Blue Complexes by Elution from Cellulose Acetate Utilizing Different MgCl$_2$ Concentrations," L. Hronowski and T. Anastassiades, *Analytical Biochemistry*, vol. 107, pp. 393-405 (1980).

Primary Examiner—Robert J. Hill, Jr.
Attorney, Agent, or Firm—Michael L. Dunn

[57] ABSTRACT

A method for detecting characteristic markers of disease in biological fluids including the steps of applying the biological fluid containing the marker onto a support matrix; differential staining with a staining mixture, selective for the marker and directly detecting the characteristic marker of disease.

21 Claims, No Drawings

METHOD FOR DETECTING CHARACTERISTIC MARKERS OF DISEASE IN BIOLOGICAL FLUIDS

BACKGROUND OF THE INVENTION

The search for improved methods for detecting and identifying characteristic markers of a wide variety of diseases, including destructive connective tissue diseases such as periodontal disease and rheumatoid arthritis, is an ongoing one.

Release of specific tissue constituents into biological fluids generally occurs due to normal tissue turnover. In disease, excessive release may occur such that tissue constituents may serve as markers of active disease. Examples of characteristic markers which may be detected by this method include glycosaminoglycans, specific proteins, etc. The glycosaminoglycans of interest may include hyaluronic acid, a variety of chondroitin sulfates, etc.

Glycosaminoglycans (GAG) (hexuronate-containing heteropolysaccharides) are polyanionic constituents of proteoglycans, which are characteristic components of connective tissues in the body. The use of GAG as a cancer-specific marker is discussed in U.S. Pat. No. 4,468,465. In this patent, a cellulose acetate membrane electrophoresis method was utilized to study the GAG. By using a combination of an electric field and appropriate electrolytes, GAG were separated according to their charge densities or backbone structures.

It has also been postulated that specific GAG in human gingival crevicular fluid are characteristic markers of periodontal disease, the destruction of tooth-supporting tissues. Periodontal disease activity has been correlated with the presence of GAG using electrophoresis, (K. S. Last, J. B. Stanbury and G. Embery, "Glycosaminoglycans in Human Gingival Crevicular Fluid as Indicators of Active Periodontal Disease", *Archives of Oral Biology*, Vol. 30, No. 3, pp. 275–281 (1985)). The method disclosed by Last, et al. included collecting gingival crevicular fluid by capillary action into 2 or 5 µl pipettes, then applying the samples to sheets of cellulose acetate, which were then subjected to electrophoresis. After electrophoresis the cellulose acetate sheets were stained using Alcian blue. A similar method of characterizing the GAG by staining and electrophoresis was disclosed in L. Hronowski and T. Anastassiades, "Characterization of Glycosaminoglycan-Alcian Blue Complexes by Elution from Cellulose Acetate Utilizing Different $MgCl_2$ Concentrations", *Analytical Biochemistry*, Vol. 107, pp. 393–405 (1980).

The procedures referenced above require specialized equipment, a certain degree of expertise and a substantial wait before results are available.

Therefore, there still exists a need for a simple, relatively fast method for detecting and identifying characteristic markers of diseases including destructive connective tissue diseases such as periodontal disease and rheumatoid arthritis.

SUMMARY OF THE INVENTION

The invention involves a method of detecting characteristic markers of disease which comprises the steps of:
a) applying biological fluid containing the marker onto a support matrix;
b) differential staining with a staining mixture, selective for the marker; and
c) directly detecting the characteristic marker.

Therefore, it is an object of this invention to provide a simple, relatively fast method for detecting and identifying characteristic markers of disease including destructive connective tissue diseases such as periodontal disease and rheumatoid arthritis.

It is a further object of this invention to provide a permanent record of the results.

DETAILED DESCRIPTION OF THE INVENTION

Characteristic markers of disease are tissue specific constituents in biological fluids which are indicative of tissue breakdown. The concentration of these characteristic markers may be enhanced during disease. The term, characteristic marker of disease, as used herein may be further defined as including those constituents which may be supported on insoluble matrices for analysis. Examples of characteristic markers which may be detected by this method include glycosaminoglycans. The glycosaminoglycans of interest may include hyaluronic acid and a variety of chondroitin sulfates.

A sufficient amount of biological fluid is applied to a support matrix. The biological fluid may be any fluid containing specific tissue constituents which may be detected by the method in accordance with this invention. Examples of such biological fluids include, but are not limited to, gingival crevicular fluid and synovial fluid. The application may be by direct collection from the patient onto the support matrix or by application of the biological fluid from a sample holder to the support matrix. Where the application is by direct collection, the support matrix should be placed in an appropriate position to allow capillary absorption of the fluid onto the matrix. Any method of direct collection, known to those skilled in the art, is suitable. The direct collection may include the step of stimulation prior to collection. The application method utilized should allow sufficient amounts of the biological fluid to be applied to the support matrix which will enable staining in accordance with this invention. Generally microliter amounts are suitable.

Support matrix as used herein means an appropriate material that will bind the characteristic marker of interest when exposed thereto and which allows differential staining thereafter. The binding may occur directly from a fluid, upon drying or otherwise. Examples of suitable matrices for the test method include cellulose acetate, filter paper and transblot membranes. The support matrix may be any suitable size or shape to apply the biological fluid thereon in accordance with the invention. The sample may then be tested immediately (subject to differential staining) or stored under suitable conditions which will not interfere with the subsequent analysis.

Differential staining as used herein means that the characteristic marker of interest is selectively stained using the critical electrolyte concentration. The critical electrolyte concentration is the concentration of electrolyte at which staining of polyions of interest, e.g. GAG, can be detected and above which staining is abolished. For differential staining, the support matrix is placed in a staining mixture, selective for the marker, for a sufficient time to allow interaction between the marker of interest and the staining mixture such that the marker is selectively stained.

The staining mixture comprises an appropriate cationic or anionic dye, a buffer and a salt providing suitable ions capable of competing with the dye for sites on the characteristic markers. Cationic dyes are positively charged ligands that interact with negatively charged substrates. Conversely, anionic dyes are negatively charged ligands that interact with positively charged substrates. Examples of suitable cationic dyes include but are not limited to Alcian blue, Alcec blue and Cupromeronic blue. Examples of anionic dyes include, but are not limited to, Biebrich Scarlet, Crocein Scarlet, Acid Fuchsin and Fast Green FCF. Buffers are substances which maintain the pH for optimal differential staining of the characteristic marker of interest. Examples of suitable buffers are acetate, citric acid-phosphate and glycine-sodium hydroxide buffers. Examples of suitable competing salts are magnesium chloride, magnesium acetate and choline chloride.

Other compatible components may be added to the staining mixture in order to enhance the selectivity of the staining such that the characteristic markers of interest are exclusively stained. Compatible means that such components will not interfere with the staining and/or the integrity of the support matrix. Examples of compatible components include ethanol and dimethylsulfoxide (DMSO).

After staining, the matrix is drained and immersed in a rinse solution, which contains all the components of the staining mixture except the dye, such that excess dye is removed. The matrix may be agitated to aid in the removal of the excess dye. In addition, a subsequent rinse step in a second rinse solution may be used to remove excess dye. The second rinse solution may comprise 50%v/v aqueous ethanol or other suitable solution known to those skilled in the art.

The invention is based on the Critical Electrolyte Concentration principle (CEC) which states: there is a critical maximum concentration of electrolyte at which staining of polyions of interest, e.g. GAG, can be detected and above which staining is abolished. By appropriate adjustment of electrolyte concentrations, differential and selective staining in mixtures of polyions is possible.

Based on the CEC principle, markers of interest can then be directly detected. By direct detection is intended to mean that additional steps of subjecting the matrices, having the biological fluid thereon, to supplemental procedures, such as electrophoresis, is not necessary.

In addition, upon differential staining and detection of the characteristic markers, these results may be used for quantitative analysis. If the amount of the characteristic marker is of interest, the results may be quantitated by a suitable method compatible with the matrix technique. Generally, it has been found that the intensity of the stain is proportional to the concentration of the characteristic marker within a certain range.

The following is a general application of the procedure for detecting glycosaminoglycans in gingival crevicular fluid (GCF). The fluid is collected directly onto an appropriate support matrix placed extracrevicularly such that the fluid is absorbed directly onto the support matrix. Amounts of the fluid which will contain amounts of the compound of interest that exceed the limit of sensitivity and enable staining in accordance with the invention are sufficient. Generally microliter amounts of GCF are suitable for detection of GAG. The support matrix may be any suitable size to collect the gingival crevicular fluid directly thereon in accordance with the invention.

The sample is allowed to dry upon the matrix and may then be tested immediately or stored under suitable conditions which will not interfere with the subsequent testing. For staining, the matrix is placed in an optimally adjusted staining mixture (optimally adjusted for sensitive and specific staining of the markers of interest) for a sufficient time to allow maximum interaction between the glycosaminoglycans and the stain. The staining mixture is as discussed above. By varying the concentrations of salts in the dye solutions, differential staining, and thus the identification of specific glycosaminoglycans can be accomplished.

The supporting matrices are drained and rinsed in solutions such that all excess dye can be removed (described above). The matrices may be agitated to aid in the removal of the excess dye.

The glycosaminoglycans can be detected directly. By direct detection is intended to mean that additional steps of subjecting the matrices, having biological fluid applied thereon, to any auxiliary procedures, such as electrophoresis, is not necessary.

By the use of this invention, recurrence of disease after treatment or onset of disease at the internal control site may be detected much sooner than possible with currect clinical procedures. Recurrence or onset of disease would be indicated by staining resembling that of a diseased site prior to maintenance. This is feasible because the invention provides a permanent record.

The following examples and preparations describe the manner and process of making and using the invention and set forth the best mode contemplated by the inventors of carrying out the invention, but are not to be construed as limiting.

EXAMPLE 1: SITE-SPECIFIC, DIRECT COLLECTION OF SAMPLE ON MATRIX

The interdental papilla adjacent to the selected dental site of interest was stimulated mechanically. Gingival crevicular fluid from the specific dental site was then collected for 30 seconds by capillary absorption onto the porous surface of a cellulose acetate strip (3 X 12 mm) placed extracrevicularly. The strip was positioned such that the nonporous surface was contacting the enamel of the tooth. Each strip was prelabelled at the top on its porous surface, for identification purposes prior to fluid collection. A sample was also collected, in the same manner, from the healthiest periodontal site in the patient as an internal control. The selection of the control site was based on standard clinically defined parameters of periodontal health. Each strip was air dried and placed in a labeled screw-capped vial for immediate testing.

For testing, the acetate strips with the absorbed fluid were covered with a staining mixture and left undisturbed for one hour at room temperature. The staining mixture was composed of 0.05%(w/v) Alcian Blue in 50% (v/v) ethanol - 25 mM acetate buffer, pH 3, containing 1 M $MgCl_2$. The strips were drained, transferred to a rinse bath and covered with a rinse solution composed of 50% (v/v) ethanol −25 mM acetate buffer, pH 3, containing 1 M $MgCl_2$. Strips to which appropriate specific glycosaminoglycan (GAG) standards had been applied were processed simultaneously with the crevicular fluid samples. The strips were next gently agitated until all the excess dye had been removed. This was determined from the blank portions of the strips to which a standard GAG had been applied. The strips were then rinsed twice in 50% (v/v) aqueous ethanol for two minutes each time, placed on bibulous paper and air dried for 10 minutes. The dried strips were stored in capped vials, protected from light at room temperature. These strips provide a permanent record.

Results

The presence or absence of stain, and the relative intensity of the stain, was determined on dried strips by visual inspection. The intensity of the stain was assigned to a scale ranging from 1+ to 4+; 1+ indicating stain just above background level and 4+, the most intense staining. The staining intensities of samples from diseased sites were compared to that of the internal control site and to those of the standard GAG.

At the time of initial diagnosis of disease, the healthiest periodontal site in the patient, as determined by clinical evaluation, was designated the internal control. There is generally a background level of metabolic turnover of glycosaminoglycans even in healthy sites and this can vary between patients. The use of an internal control within each patient overcomes problems associated with these differences in basal metabolism of glycosaminoglycans.

The periodontal disease status over the course of treatment was then assessed by comparing the staining of diseased sites with that of the untreated internal control. Successful treatment of disease was determined when staining of all diseased sites matched that of the internal control. The staining intensity of the internal control was found to remain unchanged throughout a three month treatment period in preliminary clinical studies.

EXAMPLE 2: MANUAL APPLICATION OF SAMPLE TO SUPPORT MATRIX

Samples of synovial fluid collected from a large number of patients with a variety of joint disorders were distributed in aliquots for freezing and stored at $-70°$ C. The stored samples were thawed and two-fold serial dilutions in water were prepared. Two microliter aliquots were spotted manually, on a $9 \times 12$ cm sheet of Zeta-Probe transblot membrane in order, from the most to the least concentrated. Dilutions covering the range 2 to 128-fold, or 8 to 512-fold, were spotted on a single sheet in a single column for each sample. Each sheet also contained serial dilutions of specific GAG standards.

The samples on the sheet were air dried for 10 minutes, the sheet was immersed in a bath containing the staining mixture. The entire sheet was carried through the staining procedure employing the critical electrolyte concentration principle in order to differentially stain sulfated glycosaminoglycans, specifically chondroitin-6-sulfate (C-6-S) The staining mixture was composed of 0.05%(w/v) Alcian Blue in 50% (v/v) ethanol - 25 mM acetate buffer, pH 3, containing 1M $MgCl_2$. The bath was agitated gently at room temperature for 60 minutes to allow maximum staining to occur. The staining mixture was decanted and replaced with a rinse solution containing all the components of the staining mixture except the dye. Excess dye was removed from the supporting membrane by three rinses of 1 minutes each. The membrane was finally agitated in a mixture of 50% ethanol in water three more times for complete removal of the excess dye.

Results

The method used in the above example was adapted to screen samples from patients with a variety of joint disorders. An attempt was made to determine the severity of disease on the basis of the quantity of C-6-S present in the synovial fluid. Quantitation was based in this case on the results seen by visual inspection. Designation of the highest dilution before the loss of staining was taken to indicate the relative concentration of the GAG stained. That is, the greater the dilution before loss of staining, the greater the amount of GAG present in the sample.

The staining procedure was accomplished on coded samples such that the analysis was conducted in a blind manner which precluded bias in the scoring of the stain intensities. It was found by the use of this invention that widely different amounts of C-6-S could be detected in patients within a given disease group. This would be consistent with the concept that the concentration of a specific tissue marker within extracellular fluid could be correlated with severity of disease.

In the absence of an internal control, quantitative comparison to known concentrations of standards becomes very important. The invention lends itself to this comparison as shown in this example. An alternative or independent comparison could be made to a baseline sample taken at the patient's first visit.

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

What is claimed is:

1. A method of detecting a characteristic marker of disease which comprises the steps of:
   a) applying biological fluid containing the marker onto a support matrix;
   b) differentially staining the biological fluid on the support matrix with a staining mixture, selective for the marker, using a critical electrolyte concentration technique; and
   c) directly detecting the characteristic marker, wherein the method is carried out in the absence of electrophoresis.

2. The method as recited in claim 1 wherein the fluid is dried upon the support matrix to bind the marker to the support matrix.

3. The method as recited in claim 2 wherein the biological fluid is selected from the group consisting of gingival crevicular fluid and synovial fluid.

4. The method as recited in claim 3 wherein the support matrix is selected from the group consisting of cellulose acetate, filter paper and transblot membranes.

5. The method as recited in claim 4 wherein the staining mixture comprises a dye, a buffer and a salt; wherein said salt provides suitable ions capable of competing with the dye.

6. The method as recited in claim 5 wherein the dye is a cationic dye.

7. The method as recited in claim 5 wherein the dye is an anionic dye.

8. The method as recited in claim 6 wherein the cationic dye is selected from the group consisting of Alcian blue, Alcec Blue, Cupromeronic blue.

9. The method as recited in claim 7 wherein the anionic dye is selected from the group consisting of Biebrich Scarlet, Crocein Scarlet, Acid Fuchsin, Fast Green FCF.

10. The method as recited in claim 5 wherein the buffer is an acetate buffer.

11. The method as recited in claim 8 wherein the buffer is an acetate buffer.

12. The method as recited in claim 9 wherein the buffer is an acetate buffer.

13. The method a recited in claim 5 wherein the salt is selected from the group consisting of magnesium chloride, magnesium acetate, choline chloride.

14. The method as recited in claim 6 wherein the salt is selected from the group consisting of magnesium chloride, magnesium acetate, choline chloride.

15. The method as recited in claim 7 wherein the salt is selected from the group consisting of magnesium chloride, magnesium acetate, choline chloride.

16. The method as recited in claim 10 wherein the salt is selected from the group consisting of magnesium chloride, magnesium acetate, choline chloride.

17. The method as recited in claim 5 wherein the staining mixture further comprises a compatible component for enhancing the selectivity of staining.

18. The method as recited in claim 17 wherein the compatible component is selected from the group consisting of ethanol, DMSO.

19. The method as recited in claim 2 wherein the step of staining further comprises the step of rinsing the support matrix in a rinse solution.

20. The method as recited in claim 19 wherein the rinse solution comprises the buffer and the salt used in the staining mixture.

21. The method as recited in claim 5 wherein the support matrix is placed in the staining mixture for a sufficient time to stain the characteristic marker.

* * * * *